(12) United States Patent
Heckroth et al.

(10) Patent No.: US 9,051,410 B2
(45) Date of Patent: Jun. 9, 2015

(54) POLYUREA-BASED FABRIC GLUE

(75) Inventors: Heike Heckroth, Odenthal (DE);
Hartmut Nefzger, Pulheim (DE);
Christoph Eggert, Köln (DE)

(73) Assignee: Medical Adhesive Revolution GmbH, Aachen (DE)

( * ) Notice: Subject to any disclaimer, the term of this patent is extended or adjusted under 35 U.S.C. 154(b) by 39 days.

(21) Appl. No.: 13/384,295

(22) PCT Filed: Jul. 6, 2010

(86) PCT No.: PCT/EP2010/004106
§ 371 (c)(1),
(2), (4) Date: Mar. 26, 2012

(87) PCT Pub. No.: WO2011/006606
PCT Pub. Date: Jan. 20, 2011

(65) Prior Publication Data
US 2012/0178847 A1  Jul. 12, 2012

(30) Foreign Application Priority Data
Jul. 16, 2009 (EP) .................................... 09009248

(51) Int. Cl.
| C08L 75/02 | (2006.01) |
| C08L 75/04 | (2006.01) |
| C09D 175/02 | (2006.01) |
| C08G 18/10 | (2006.01) |
| A61L 24/04 | (2006.01) |
| C08G 18/18 | (2006.01) |
| C09J 175/12 | (2006.01) |

(52) U.S. Cl.
CPC ............... *C08G 18/10* (2013.01); *A61L 24/046* (2013.01); *C08G 18/18* (2013.01); *C09J 175/12* (2013.01)

(58) Field of Classification Search
None
See application file for complete search history.

(56) References Cited

U.S. PATENT DOCUMENTS

| 3,479,310 A * | 11/1969 | Bayer et al. .................... 524/591 |
| 3,615,744 A * | 10/1971 | Yokoo et al. ................. 106/18.31 |
| 3,886,122 A * | 5/1975 | Fabris et al. .................... 528/53 |
| 4,040,992 A * | 8/1977 | Bechara et al. ................ 521/117 |
| 4,190,566 A * | 2/1980 | Noll et al. ..................... 524/839 |
| 4,334,944 A * | 6/1982 | Creyf ......................... 156/308.2 |
| 4,396,766 A * | 8/1983 | Farmer et al. ..................... 546/6 |
| 4,501,852 A * | 2/1985 | Markusch et al. ............. 524/591 |
| 4,587,149 A * | 5/1986 | Murachi ......................... 428/90 |
| 4,774,080 A * | 9/1988 | Yamamori et al. ......... 424/78.09 |
| 4,918,147 A * | 4/1990 | Yamamori et al. ......... 424/78.09 |
| 5,057,153 A * | 10/1991 | Ruggiero .................... 106/18.33 |
| 5,080,892 A * | 1/1992 | Yamamori et al. ......... 424/78.09 |
| 5,098,473 A * | 3/1992 | Hani et al. ................. 106/18.33 |
| 5,112,397 A * | 5/1992 | Farmer et al. .............. 106/18.33 |
| 5,126,170 A * | 6/1992 | Zwiener et al. ............. 427/385.5 |
| 5,137,569 A * | 8/1992 | Waldron et al. ............ 106/18.33 |
| 5,185,033 A * | 2/1993 | Hani et al. ................. 106/18.33 |
| 5,232,493 A * | 8/1993 | Waldron et al. ............ 106/18.33 |
| 5,236,741 A * | 8/1993 | Zwiener et al. ............. 427/385.5 |
| 5,238,490 A * | 8/1993 | Farmer et al. .............. 106/18.33 |
| 5,243,012 A * | 9/1993 | Wicks et al. ..................... 528/58 |
| 5,246,489 A * | 9/1993 | Farmer et al. .............. 106/18.33 |
| 5,252,123 A * | 10/1993 | Hani et al. ................. 106/18.33 |
| 5,298,061 A * | 3/1994 | Waldron et al. ............ 106/18.33 |
| 5,342,437 A * | 8/1994 | Gavin et al. ................ 106/18.33 |
| 5,397,930 A * | 3/1995 | Nilssen ......................... 307/150 |
| 5,540,860 A * | 7/1996 | Hosseini et al. ................ 516/66 |
| 5,594,097 A * | 1/1997 | Chaffanjon et al. .......... 528/419 |
| 5,650,095 A * | 7/1997 | Hosseini et al. ................ 516/77 |
| 5,736,604 A * | 4/1998 | Luthra ......................... 524/591 |
| 5,880,173 A * | 3/1999 | Matsuda et al. ............. 523/122 |
| 5,925,781 A * | 7/1999 | Pantone et al. ................ 560/26 |
| 6,017,562 A * | 1/2000 | Kaufman et al. ............. 424/489 |
| 6,359,101 B1 * | 3/2002 | O'Connor et al. ............. 528/66 |
| 6,458,293 B1 * | 10/2002 | Roesler et al. ........... 252/182.23 |
| 6,482,333 B1 * | 11/2002 | Roesler et al. ........... 252/182.12 |
| 7,022,750 B2 * | 4/2006 | Camp et al. ................... 523/177 |
| 7,335,248 B2 * | 2/2008 | Abou-Nemeh ............ 106/18.34 |
| 7,435,771 B2 * | 10/2008 | Lei et al. ...................... 524/287 |
| 7,455,851 B1 * | 11/2008 | Nelson et al. ................ 424/406 |
| 7,659,397 B2 * | 2/2010 | Hidaka ............................ 546/6 |
| 7,691,938 B2 * | 4/2010 | Finnie ......................... 524/556 |
| 7,942,958 B1 * | 5/2011 | Gavin et al. ................ 106/18.36 |
| 8,168,431 B2 * | 5/2012 | Brady et al. ................. 435/396 |
| 2002/0110575 A1 * | 8/2002 | Gavin et al. ................ 424/408 |
| 2003/0135238 A1 * | 7/2003 | Milbocker .................... 606/231 |
| 2003/0215522 A1 * | 11/2003 | Johnson et al. .............. 424/642 |
| 2004/0058855 A1 * | 3/2004 | Schwartz et al. ................ 514/6 |
| 2004/0067315 A1 * | 4/2004 | Niesten et al. ............. 427/372.2 |
| 2004/0157945 A1 * | 8/2004 | Barber ......................... 521/155 |
| 2004/0191331 A1 * | 9/2004 | Schwartz et al. ............. 424/641 |
| 2005/0129733 A1 * | 6/2005 | Milbocker et al. ........... 424/423 |
| 2005/0252408 A1 * | 11/2005 | Richardson et al. ....... 106/15.05 |
| 2006/0058410 A1 * | 3/2006 | Yu et al. ....................... 521/155 |
| 2006/0148977 A1 * | 7/2006 | Finnie ......................... 524/556 |
| 2007/0003594 A1 * | 1/2007 | Brady et al. ................. 424/426 |
| 2007/0110700 A1 * | 5/2007 | Wells et al. ................ 424/70.21 |
| 2008/0067720 A1 * | 3/2008 | Wiese et al. ................. 264/334 |
| 2009/0012206 A1 * | 1/2009 | Heckroth et al. ............ 523/111 |
| 2010/0021530 A1 * | 1/2010 | Weinfield .................... 424/449 |
| 2010/0028391 A1 * | 2/2010 | Okawa et al. ................ 424/401 |

FOREIGN PATENT DOCUMENTS

| DE | 69311633 T2 | 10/1997 |
| DE | 10246708 A1 | 4/2004 |
| EP | 1277876 A2 * | 1/2003 |
| EP | 2011808 A1 | 1/2009 |
| EP | 2062603 A1 | 5/2009 |

* cited by examiner

*Primary Examiner* — James J Seidleck
*Assistant Examiner* — Peter A Salamon
(74) *Attorney, Agent, or Firm* — Drinker Biddle & Reath LLP

(57) ABSTRACT

The present invention relates to a polyurea system, the use of such a polyurea system for sealing, linking, gluing, or covering of cellular tissue, and a dosing system having two chambers for a polyurea system such as this. The polyurea system comprises as components: A) an isocyanate-functioning prepolymer, which can be derived by reacting aliphatic isocyanates with polyoles, and B) an amino-functioning ester of aspartic acid. According to the invention, water and/or tertiary amine is added to the system, in order to increase the reacting speed of the prepolymer with the amino-functioning ester of aspartic acid while decreasing the setting time at the same time.

13 Claims, No Drawings

POLYUREA-BASED FABRIC GLUE

RELATED APPLICATIONS

This application is a national stage application (under 35 U.S.C. §371) of PCT/EP2010/004106, filed Jul. 6, 2010, which claims benefit of European Application No. 09009248.7, filed Jul. 16, 2009.

The present invention relates to a polyurea system, to the use of a polyurea system of this kind for sealing, connecting, bonding or covering cellular tissue, and to a metering system having two chambers for a polyurea system of this kind.

A variety of materials which are used as tissue adhesives are available commercially. They include the cyanoacrylates Dermabond® (octyl 2-cyanoacrylate) and Histoacryl Blue® (butyl cyanoacrylate). A prerequisite for efficient bonding of the cyanoacrylates are dry substrates. In cases of severe bleeding, adhesives of this kind fail.

Available alternatives to the cyanoacrylates are biological adhesives such as, for example, BioGlue®, a mixture of glutaraldehyde and bovine serum albumin, various collagen-based and gelatine-based systems (FloSeal®), and the fibrin adhesives (Tissucol). These systems serve primarily to staunch blood (haemostasis). Apart from the high costs, fibrin adhesives are notable for a relatively weak adhesive strength and a rapid breakdown, and so can be used only in cases of relatively minor injury on unstretched tissue. Collagen-based and gelatine-based systems such as FloSeal® serve exclusively for haemostasis. Moreover, because fibrin and thrombin are obtained from human material, and collagen and gelatine from animal material, there is always a risk of infection with biological systems. Biological materials, furthermore, must be given refrigerated storage, and so their use in emergency care such as in disaster zones, for example, or in the case of military deployments, etc., is not possible. Here, for the treatment of traumatic wounds, there are QuikClot® or QuikClot ACS+™ available, QuikClot being a granular mineral which in an emergency is introduced into the wound, where it leads to coagulation as a result of removal of water. In the case of QuikClot® this is a highly exothermic reaction, leading to burns. QuikClot ACS+™ is a gauze into which the salt has been embedded. For staunching blood, the system must be pressed firmly onto the wound.

From EP 2 011 808 A1, the preparation and use of polyurea systems as tissue adhesives is known in principle. The systems disclosed therein comprise at least two components. There, A) is an isocyanate-functional prepolymer obtainable by reacting aliphatic isocycanates with polyols, and B) is an amino-functional aspartic ester. In addition or alternatively to these components it is also possible for there to be present, as component C), reaction products of isocyanate-functional prepolymers with aspartic esters as for component B). Optionally there may also be organic fillers D) present that have a viscosity at 23° C., measured in accordance with DIN 53019, in the range from 10 to 6000 mPas.

The amino-functional aspartic ester has the following general formula

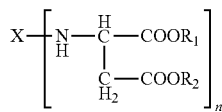

(I)

where X is an organic radical containing no Zerewitinoff-active hydrogen, $R_1$ and $R_2$ are identical or different organic radicals containing no Zerewitinoff-active hydrogen, and n is an integer of at least 2.

With regard to the definition of Zerewitinoff-active hydrogen, reference is made to the corresponding definition in Römpp Chemie Lexikon, Georg Thieme Verlag, Stuttgart. For the purposes of this specification, groups with Zerewitinoff-active hydrogen are understood to be more particularly OH, NH or SH.

The 2-component polyurea systems disclosed can be used as tissue adhesives for sealing wounds in associations of human and animal cells. There it is possible to achieve a very good adhesive outcome. Nevertheless it has been found that the reaction time in the reaction of the prepolymer with the amino-functional aspartic ester is not high enough in all of the systems disclosed, particularly in the case of the biodegradable polyester-based systems that are not mentioned in the working examples, thereby resulting in undesirably long curing times of more than 6 minutes. By curing time is meant the time within which tissue adhesive joins two sections of tissue to one another in such a way that they can no longer be separated from one another by gentle pulling, or the time after which a bleed is staunched following application of the tissue adhesive. The problem of excessive curing times occurs in particular in the case of systems whose prepolymers are based on polyesters. A low curing time of less than 2 minutes, however, is necessary especially in order, for example, to prevent higher blood loss. On the other hand, the systems must also not react too quickly (<20 s), in order to ensure that they can be applied.

It was an object of the invention, therefore, to improve the 2-component system of EP 2 011 808 in such a way that even when using ester-based prepolymers, a high rate of reaction with the amino-functional aspartic ester and hence a short cure time can be realized. An additional condition to be observed here was that the cured system in accordance with ISO 10993 must not exhibit any cytotoxicity when administered to humans.

This object has been achieved in accordance with the invention by adding water and/or tertiary amine to the polyurea systems known from EP 2 011 808 A1.

It has been found that simply by adding just either water or tertiary amine, the reaction rate of the prepolymer with the amino-functional aspartic ester is significantly increased and hence the cure time is reduced. Surprisingly, the curing time rises even more if both water and tertiary amine are added together. Hence the reaction rate is increased further by a factor of around 1.3 if a combination of water and tertiary amine is used, rather than a corresponding amount of only one of the two substances.

According to one preferred embodiment, the polyurea system comprises tertiary amines of the general formula

(II)

where $R_3$, $R_4$ and $R_5$ independently of one another may be alkyl or heteroalkyl radicals having heteroatoms in the alkyl chain or at the end thereof, or $R_3$ and $R_4$, together with the nitrogen atom carrying them, may form an aliphatic, unsaturated or aromatic heterocycle, which may optionally contain further heteroatoms.

Particular preference is given to tertiary amines selected from the group of triethanolamine, tetrakis(2-hydroxyethyl)ethylenediamine, N,N-dimethyl-2-(4-methylpiperazin-1-yl)ethanamine, 2-{[2-(dimethylamino)ethyl](methyl)amino}-ethanol, and 3,3',3''-(1,3,5-triazinane-1,3,5-triyl)tris(N,N-dimethylpropan-1-amine).

The concentration of the water in the polyurea system may in particular be 0.2% to 2.0% by weight. On addition of 0.2% by weight of water, the average reaction rate increases by a factor of 2. If 2.0% by weight of water is added, there is an increase in the reaction rate by a factor of 8.

It is possible to add in particular 0.1% to 1.0% by weight of tertiary amine to the polyurea system. In this case the addition of 0.1% by weight produces a doubling in the average reaction rate, and the addition of 1.0% by weight leads to an increase by a factor of 2.5.

According to one further preferred embodiment, X is an optionally branched or linear organic radical having 1 to 20, preferably 2 to 10, carbon atoms and more preferably a C3, C4, C5 or C6 radical which optionally carries heteroatoms.

The polyols A2) may comprise preferably polyester polyols and/or polyester-polyether polyols and/or polyether polyols, more particularly having an ethylene oxide fraction of between 60% and 90% by weight.

The polyols A2) may preferably have a number-average molecular weight of 2000 to 8500 g/mol.

The organic fillers of component C) may preferably be hydroxyl-functional compounds, more particularly polyether polyols. The fillers of component C) here may have an average OH functionality of 1.5 to 3, preferably of 1.8 to 2.2, and with particular preference of 2. The fillers of component C), in a further-preferred embodiment, may contain repeating ethylene oxide units.

A second aspect of the present invention relates to the use of the polyurea systems for sealing, connecting, bonding or covering cellular tissue, more particularly for staunching the egress of blood or tissue fluids or for sealing leaks in cellular tissue. Thus it has emerged that the polyurea systems of the invention are especially suitable for connecting, bonding or covering human or animal cellular tissue. They can be used to produce adhesive sutures that cure rapidly, adhere strongly to the tissue and are transparent, flexible and biocompatible.

Subject matter of the invention, thirdly, is a metering system having two chambers for a polyurea system of the invention, comprising in one chamber component A) and in the other chamber components B) and E), and also optionally components B), D)+E), and also optionally components C) and D) with, where used, E) of the polyurea system.

The amino-functional polyaspartic esters B) are prepared in a known way by reaction of the corresponding primary, at least difunctional, amines $X(NH_2)_n$ with maleic or fumaric esters of the general formula

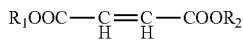

Preferred maleic or fumaric esters are dimethyl maleate, diethyl maleate, dibutyl maleate and the corresponding fumaric esters.

Preferred primary, at least difunctional, amines $X(NH_2)_n$ are ethylenediamine, 1,2-diaminopropane, 1,4-diaminobutane, 1,3-diaminopentane, 1,5-diaminopentane, 2-methyl-1,5-diaminopentane, 1,6-diaminohexane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethyl-cyclohexane, 2,4- and/or 2,6-hexahydrotolylenediamine, 2,4'- and/or 4,4'-diaminodicyclohexylmethane, 3,3'-dimethyl-4,4'-diaminodicyclohexylmethane, 2,4,4'-triamino-5-methyl-dicyclohexylmethane and polyetheramines having aliphatically attached primary amino groups, with a number-average molecular weight $M_n$ of 148 to 6000 g/mol.

Particularly preferred primary, at least difunctional, amines are 1,3-diaminopentane, 1,5-diaminopentane, 2-methyl-1,5-diaminopentane, 1,6-diaminohexane, 1,13-diamino-4,7,10-trioxamidecane. 2-Methyl-1,5-diaminopentane is especially preferred.

In one preferred embodiment of the invention $R_1=R_2=$ethyl, with X being based on 2-methyl-1,5-diaminopentane as the n-functional amine.

The preparation of the amino-functional aspartic esters A) from the stated starting materials is accomplished in accordance with DE-A 69 311 633 preferably within the temperature range from 0 to 100° C., the starting materials being employed in proportions such that for each primary amino group there is at least one, preferably precisely one, olefinic double bond, and, after the reaction, any starting materials used in excess can be separated off by distillation. The reaction may take place in bulk or in the presence of suitable solvents such as methanol, ethanol, propanol or dioxane or mixtures of such solvents.

The systems of the invention are obtained by mixing the prepolymers (A) with the amino-functional aspartic esters B) and also, optionally, with the components C) and/or D). The ratio of free or blocked amino groups to free NCO groups is preferably 1:1.5, more preferably 1:1. Water and/or amine here are admixed to component B and/or C.

Immediately after the mixing of the individual components with one another, the systems of the invention possess a shear viscosity at 23° C., measured in accordance with DIN 53019, of preferably 500 to 20 000 mPas, more preferably 500 to 8000 mPas.

The isocyanate-functional prepolymers used in A) are obtainable by reacting isocyanates A1) with polyols B2), optionally with addition of catalysts and also auxiliaries and additives.

Examples of isocyanates which can be used are monomeric aliphatic or cycloaliphatic di- or triisocyanates such as 1,4-butylene diisocyanate (BDI), 1,6-hexamethylene diisocyanate (HDI), isophorone diisocyanate (IPDI), 2,2,4- and/or 2,4,4-trimethylhexamethylene diisocyanate, the isomeric bis(4,4'-isocyanatocyclohexyl)methanes or their mixtures of any desired isomer content, 1,4-cyclohexylene diisocyanate, 4-isocyanatomethyl-1,8-octane diisocyanate (nonane triisocyanate), and also alkyl 2,6-diisocyanatohexanoate (lysine diisocyanate) with C1-C8 alkyl groups.

Besides the abovementioned monomeric isocyanates it is also possible to use their higher molecular mass derivatives with uretdione, isocyanurate, urethane, allophanate, biuret, iminooxadiazinedione or oxadiazinetrione structure and also mixtures thereof.

In A) it is preferred to use isocyanates of the aforementioned kind having exclusively aliphatically or cycloaliphatically attached isocyanate groups or mixtures thereof.

With very particular preference, hexamethylene diisocyanate is used in A).

The polyols used in A) may be polyether polyols and polyether esters. The pre-polymers synthesized therefrom are liquid at room temperature and have a shear viscosity at 23° C., measured in accordance with DIN 53019, of 200 to 10 000 mPas, preferably 400 to 6000 mPas.

Polyether ester polyols of this kind are prepared in accordance with the prior art preferably by polycondensation of polycarboxylic acids, anhydrides of polycarboxylic acids, and also esters of polycarboxylic acids with volatile alcohols, preferably C1 to C6 monools, such as methanol, ethanol, propanol or butanol, with a molar excess of low molecular weight and/or higher molecular weight polyol; as polyol, use is made of polyols containing ether groups, optionally in mixtures with other polyols free from ether groups.

For the polyether ester synthesis it is of course also possible to use mixtures of the polyols of low and higher molecular weight.

Such low molecular weight polyols used in molar excess are polyols having molar masses of 62 to 299 daltons, having 2 to 12 C atoms and hydroxyl functionalities of at least 2, which additionally may be branched or unbranched and whose hydroxyl groups are primary or secondary. These low molecular weight polyols may also contain ether groups. Typical representatives are ethylene glycol, propane-1,2-diol, propane-1,3-diol, butane-1,4-diol, butane-2,3-diol, 2-methyl-propane-1,3-diol, pentane-1,5-diol, hexane-1,6-diol, 3-methylpentane-1,5-diol, 1,8-octanediol, 1,10-decanediol, 1,12-dodecanediol, cyclohexanediol, diethylene glycol, triethylene glycol and higher homologues, dipropylene glycol, tripropylene glycol and higher homologues, glycerol, 1,1,1-trimethylolpropane, and also oligo-tetrahydrofuran having hydroxyl end groups. Within these groups, of course, it is also possible to use mixtures.

Polyols of higher molecular weight, in molar excess, are polyols having molar masses of 300 to 3000 daltons which are obtained by ring-opening polymerization of epoxides, preferably ethylene oxide and/or propylene oxide, and also by acid-catalyzed, ring-opening polymerization of tetrahydrofuran. For the ring-opening polymerization of epoxides it is possible to use either alkali metal hydroxides or double metal cyanide catalysts.

As starters for ring-opening epoxide polymerizations it is possible to use all molecules having a functionality of at least two, from the group of the amines and of the aforementioned low molecular weight polyols. Typical representatives are 1,1,1-trimethylolpropane, glycerol, o-TDA, ethylenediamine, propylene 1,2-glycol, etc., and also water, including mixtures thereof. Within the group of the excess, higher molecular weight polyols it is of course also possible to use mixtures.

The higher molecular weight polyols, where they are hydroxyl-terminated polyalkylene oxides of ethylene oxide and/or propylene oxide, may be constructed randomly or blockwise, with the presence of mixed blocks also being possible.

Polycarboxylic acids are not only aliphatic but also aromatic carboxylic acids, which may be cyclic, linear, branched or unbranched, and which have between 4 and 24 C atoms.

Examples are succinic acid, glutaric acid, adipic acid, azelaic acid, sebacic acid, 1,10-decanedicarboxylic acid, 1,12-dodecanecarboxylic acid, phthalic acid, terephthalic acid, isophthalic acid, trimellitic acid, pyromellitic acid. Preference is given to succinic acid, glutaric acid, adipic acid, sebacic acid, lactic acid, phthalic acid, terephthalic acid, isophthalic acid, trimellitic acid, pyromellitic acid. Particularly preferred are succinic acid, glutaric acid and adipic acid.

The group of the polycarboxylic acids also, moreover, encompasses hydroxylcarboxylic acids, and their internal anhydrides, such as caprolactone, lactic acid, hydroxybutyric acid, ricinoleic acid, etc. Also included, furthermore, are monocarboxylic acids, especially those which possess more than 10 C atoms, such as soybean oil fatty acid, palm oil fatty acid and peanut oil fatty acid, in which case their fraction does not exceed 10% by weight as a proportion of the overall reaction mixture constructing the polyether ester polyol, and, additionally, the consequent deficit functionality being compensated by using polyols having a functionality of at least three, whether among the low molecular weight polyols or the high molecular weight polyols.

Polyether ester polyol preparation takes place in accordance with the prior art at elevated temperature in the range from 120 to 250° C., initially under atmospheric pressure, later with application of reduced pressure of 1 to 100 mbar, preferably, though not necessarily, using an esterification or transesterification catalyst, the reaction being taken to a degree of completion such that the acid number drops to levels of 0.05 to 10 mg KOH/g, preferably 0.1 to 3 mg KOH/g and more preferably 0.15 to 2.5 mg KOH/g.

As part of the atmospheric pressure phase, before the application of reduced pressure, moreover, it is possible to use an inert gas. Alternatively or for individual phases of the esterification, of course, it is also possible to employ liquid or gaseous entraining agents. For example, the water of reaction can be carried off either using nitrogen as a carrier gas or using an azeotropic entraining agent, such as benzene, toluene, xylene, dioxane, etc., for example.

It is of course also possible to use blends of polyether polyols with polyester polyols in any desired proportions.

The polyester polyols used are preferably hydrophilic. The mass fraction of the total of component A) that can be traced back to ethylene oxide, preferably, is preferably 40% to 95% by weight, more preferably 60% to 90% by weight.

The polyols used preferably have an average OH functionality of 2 to 4 and a number-average molecular weight of 400 to 20 000 g/mol, more preferably 2000 to 10 000 g/mol and very preferably 4000 to 8500.

Polyether polyols are preferably polyalkylene oxide polyethers based on ethylene oxide and optionally propylene oxide.

These polyether polyols are based preferably on starter molecules with a functionality of two or more, such as difunctional or higher polyfunctional alcohols or amines.

Examples of such starters are water (considered to be a diol), ethylene glycol, propylene glycol, butylene glycol, glycerol, TMP, sorbitol, pentaerythritol, triethanolamine, ammonia or ethylenediamine.

Preferred polyalkylene oxide polyethers correspond to those of the aforementioned kind and contain from 50% to 100%, preferably 60% to 90%, of ethylene oxide-based units, based on the amounts of alkylene oxide units that are present in total.

It is likewise possible to use hydroxyl-containing polycarbonates, preferably poly-carbonate diols, having number-average molecular weights $M_n$ of 400 to 8000 g/mol, preferably 600 to 3000 g/mol. They are obtainable by reaction of carbonic acid derivatives, such as diphenyl carbonate, dimethyl carbonate or phosgene, with polyols, preferably diols.

Examples of such diols are ethylene glycol, 1,2- and 1,3-propanediol, 1,3- and 1,4-butanediol, 1,6-hexanediol, 1,8-octanediol, neopentylglycol, 1,4-bishydroxy-methylcyclohexane, 2-methyl-1,3-propanediol, 2,2,4-trimethylpentane-1,3-diol, dipropylene glycol, polypropylene glycols, dibutylene glycol, polybutylene glycols, bisphenol A and lactone-modified diols of the aforementioned kind.

For the synthesis of the prepolymer it is preferred to use polyether polyols of the aforementioned kind.

For preparing the prepolymer, the isocyanate is reacted with the polyol at an NCO/OH ratio of preferably 4:1 to 12:1, more preferably 8:1, and then the fraction of unreacted isocyanate is separated off by means of suitable methods. Typically for this purpose thin-film distillation is used, to give products low in residual monomer, having residual monomer contents of less than 1% by weight, preferably less than 0.1% by weight, very preferably less than 0.03% by weight.

During the preparation it is possible, optionally, to add stabilizers such as benzoyl chloride, isophthaloyl chloride, dibutyl phosphate, 3-chloropropionic acid or methyl tosylate.

The reaction temperature here is 20 to 120° C., preferably 60 to 100° C.

The prepolymers prepared have an average NCO content, measured in accordance with DIN EN ISO 11909, of 2% to 10% by weight, preferably 2.5% to 8% by weight.

In accordance with cytotoxicity measurement to ISO 10993, the organic liquid fillers used in D) are preferably not cytotoxic.

As organic fillers it is possible for example to use polyethylene glycols liquid at 23° C., such as PEG 200 to PEG 600, their monoalkyl and/or dialkyl ethers such as PEG 500 dimethyl ether, liquid polyether polyols and polyester polyols, liquid polyesters such as Ultramoll (Lanxess AG, Leverkusen, DE) and also glycerol and its liquid derivatives such as triacetin (Lanxess AG, Leverkusen, DE), for example.

The organic fillers of component C) are preferably hydroxyl- or amino-functional compounds, preferably purely hydroxyl-functional compounds. Preferred particularly are polyols. Preferred polyols are polyether and/or polyester polyols, more preferably polyether polyols.

The preferred organic fillers preferably possess average OH functionalities of 1.5 to 3, more preferably 1.8 to 2.2, very preferably 2.0.

The preferred organic fillers of the component preferably possess repeating units derived from ethylene oxide.

The viscosity of the organic fillers is preferably 50 to 4000 mPas, more preferably 50 to 2000 mPas, at 23° C. as measured to DIN 53019.

In one preferred embodiment of the invention polyethylene glycols are used as organic fillers. They preferably have a number-average molecular weight of 100 to 1000 g/mol, more preferably 200 to 400 g/mol.

The weight ratio of the filler component D) to the aspartate component B) is 0:1 to 20:1, preferably 0:1 to 12:1.

The weight ratio of filler, based on the total amount of the mixture of D) and B) is situated in the range from 0 to 100%, preferably 0 to 60%.

In order further to reduce the average equivalent weight of the compounds used in total for prepolymer crosslinking, based on the NCO reactive groups, it is also possible, in addition to the compounds used in A), to prepare the amino- or hydroxyl-functional reaction products of isocyanate-functional prepolymers with aspartic esters and/or organic fillers, where the latter are amino- or hydroxyl-functional, in a separate preliminary reaction and then to use them as a relatively high molecular weight curing component.

In the preliminary extension it is preferred to use ratios of isocyanate-reactive groups to isocyanate groups of 50:1 to 1, 5:1, more preferably 15:1 to 4:1.

The isocyanate-functional prepolymer to be used for this purpose may correspond to that of component A) or else, alternatively, may be constructed of the components listed as possible constituents of the isocyanate-functional prepolymers in the context of this specification.

An advantage of this modification by preliminary extension is that the equivalent weight and the equivalent volume of the curing component can be modified within clear limits. As a result, it is possible to carry out application using commercially available 2-chamber metering systems, to give an adhesive system which, with existing proportions of the chamber volumes, can be adjusted to the desired ratio of NCO-reactive groups to NCO groups.

Into the adhesive formulation it is of course also possible to incorporate active pharmacological ingredients such as
  a) analgesics with and without anti-inflammatory effect
  b) anti-inflammatory drugs
  c) substances having antimicrobial activity
  d) antimycotics
  e) antiparasitic substances.

This is described in more detail in patent application BMS 08 1 029, unpublished at the priority date of the present specification, which is hereby made subject matter of the present specification by reference.

For further components and preparation processes suitable for preparing the polyurea system, and also for the possible uses of the polyurea system, the relevant disclosure content of EP 2 011 808 A1 is hereby made part of the subject matter of the present specification by reference.

EXAMPLES

PEG 600: Polyethylene glycol of mass 600

The processing life means the time within which the polymer mixture can still be applied by means of a metering system with static mixer.

Example 1

Aspartate A

Added slowly dropwise under a nitrogen atmosphere to 2 mol of diethyl maleate was 1 mol of 2-methyl-1,5-diaminopentane, so that the reaction temperature did not exceed 60° C. This was followed by heating at 60° C. until diethyl maleate was no longer detectable in the reaction mixture. The product was used without further purification.

Example 2

Polyester A

Water was removed by distillation at 210-220° C. under atmospheric pressure over 12 hours from a stirred mixture consisting of 24.7 g of adipic acid and 281.4 g of PEG 600. Then 30 mg of tin(II) chloride were added to the mixture, and water was removed by distillation under reduced pressure for a further 24 hours, until the mixture had an acid number of less than 1.

Example 3

Polyester B

Water was removed by distillation at 210-220° C. under atmospheric pressure over 12 hours from a stirred mixture consisting of 24.7 g of adipic acid in 152.3 g of PEG 600. Then 30 mg of tin(II) chloride were added to the mixture, and water was removed by distillation under reduced pressure for a further 24 hours, until the mixture had an acid number of less than 1.

The polyesters used are dewatered by stirring at 80° C. and 0.13 mbar for one hour.

Example 4

Prepolymer A

A 1 l four-neck flask was charged with 680 g of HDI and 1.08 g of benzoyl chloride. Over the course of 2 hours, at 80°

C., 400 g of the dewatered polyester A were added and stirring was continued for an hour. Then the excess HDI was removed by thin-film distillation at 130° C. and 0.13 mbar. This gave the prepolymer with an NCO content of 5.83%. The residual monomer content was <0.03% of HDI.

Example 5

Prepolymer B

A 1 l four-neck flask was charged with 240 g of HDI and 0.53 g of benzoyl chloride. Over the course of 2 hours, at 80° C., 287.3 g of the dewatered polyester B were added and stirring was continued for an hour. Then the excess HDI was removed by thin-film distillation at 130° C. and 0.13 mbar. This gave the prepolymer with an NCO content of 3.83%. The residual monomer content was <0.03% of HDI.

Example 6

An amount of 2.6 g of aspartate A was added to 8 g of the prepolymer A, with different amounts of water and amine, and the processing life was measured.

| Triethanolamine [%] | Water [%] | Processing life |
| --- | --- | --- |
| / | / | 11 min 20 s |
| / | 0.02 | 5 min 20 s |
| / | 0.2 | 1 min 40 s |
| 0.06 | / | 10 min 10 s |
| 0.6 | / | 9 min 50 s |
| 0.6 | 0.02 | 4 min 40 s |
| 0.6 | 0.2 | 1 min 15 s |

Example 7

An amount of 1.71 g of aspartate A was added to 8 g of the prepolymer B, with different amounts of water and amine, and the processing life was measured.

| Triethanolamine [%] | Water [%] | Processing life |
| --- | --- | --- |
| / | / | 20 min |
| / | 0.02 | 8 min 30 s |
| / | 0.2 | 2 min 20 s |
| 0.06 | / | 18 min |
| 0.6 | / | 13 min 50 s |
| 0.6 | 0.02 | 6 min 30 s |
| 0.6 | 0.2 | 2 min |

Example 8

An amount of 1.08 g of aspartate A was added to 8 g of a trifunctional polyether polyol-HDI prepolymer prepared in the same way as for prepolymer A and having an NCO content of 2.37%, with different amounts of water and amine, and the processing life was measured.

| Triethanolamine [%] | Water [%] | Processing life |
| --- | --- | --- |
| / | / | 9 min 50 |
| / | 0.02 | 5 min 40 s |
| / | 0.2 | 1 min 40 s |
| 0.06 | / | 6 min 50 s |
| 0.6 | / | 5 min 50 s |
| 0.6 | 0.02 | 4 min |
| 0.6 | 0.2 | 50 s |

In all cases, no change was observed in the adhesive strength to muscle tissue.

The invention claimed is:
1. A polyurea system comprising
A) isocyanate-functional prepolymers obtained by reacting
aliphatic isocyanates A1) with
polyols A2) which have a number-average molecular weight of ≥400 g/mol and an average OH functionality of 2 to 6,
B) amino-functional aspartic esters of formula (I)

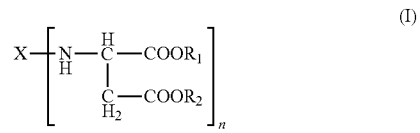

wherein
X is an organic radical containing no Zerewitinoff-active hydrogen,
$R_1$ and $R_2$
are identical or different organic radicals containing no Zerewitinoff-active hydrogen, and
n is an integer of at least 2,
and/or
optionally C) organic fillers and
optionally D) reaction products of the isocyanate-functional prepolymers of A) with aspartic esters B) and/or organic fillers C),
wherein said system comprises water and tertiary amine as E), wherein the tertiary amine is selected from the group consisting of N,N-dimethyl-2-(4-methylpiperazin-1-yl)ethanamine, 2-[{2-(dimethylamino)ethyl}(methyl)amino]ethanol, and 3,3',3"-(1,3,5-triazinane-1,3,5-triyl)tris(N,N-dimethylpropan-1-amine).
2. The polyurea system of claim 1, wherein said polyurea system contains 0.2% to 2.0% by weight of water and/or 0.1% to 1.0% by weight of tertiary amine.
3. The polyurea system of claim 1, wherein X is an optionally branched or linear organic radical having 1 to 20 carbon atoms which optionally contains heteroatoms.
4. The polyurea system of claim 1, wherein the polyols A2) comprise polyester polyols and/or polyester-polyether polyols and/or polyether polyols.
5. The polyurea system of claim 4, wherein the polyols used for preparing component A) have a number-average molecular weight of 4000 to 8500 g/mol.
6. The polyurea system of claim 1, wherein the organic fillers of component C) are hydroxyl-functional compounds.
7. The polyurea system of claim 6, wherein the fillers of component C) have an average OH functionality of 1.5 to 3.
8. The polyurea system of claim 6, wherein the fillers of component C) have repeating ethylene oxide units.
9. The polyurea system of claim 1 for sealing, connecting, bonding or covering cellular tissue, more particularly for staunching the egress of blood or tissue fluids or for sealing leaks in cellular tissue.

10. The polyurea system of claim 9 for use for sealing, connecting, bonding or covering human or animal cellular tissue.

11. A composition for sealing, connecting, bonding, or covering cellular tissue comprising the polyurea system of claim 1.

12. The composition of claim 11, wherein said composition is used for sealing, connecting, bonding or covering human or animal cellular tissue.

13. A metering system having two chambers for a polyurea system as claimed in claim 1, wherein one chamber contains component A) and the other chamber contains components B) and E) or B), D)+E), and, optionally, components C) and D) of the polyurea system.

* * * * *